United States Patent
Mueller et al.

[11] Patent Number: 6,045,779
[45] Date of Patent: *Apr. 4, 2000

[54] SKIN AND HAIR AEROSOL FOAM PREPARATIONS CONTAINING AN ALKYL POLYGLYCOSIDE AND VEGETABLE OIL

[75] Inventors: Reinhard Mueller, Erkelenz; Kurt Seidel; Anke Kaczich, both of Duesseldorf; Detlef Hollenberg, Erkrath; Iduna Matzik, Mettmann, all of Germany

[73] Assignee: Henkel Kommanditgesellschaft auf Aktien, Duesseldorf, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/693,273
[22] PCT Filed: Feb. 9, 1995
[86] PCT No.: PCT/EP95/00462
  § 371 Date: Oct. 18, 1996
  § 102(e) Date: Oct. 18, 1996
[87] PCT Pub. No.: WO95/22312
  PCT Pub. Date: Aug. 24, 1995

[30] Foreign Application Priority Data

Feb. 18, 1994 [DE] Germany ............... 44 05 127

[51] Int. Cl.$^7$ ............... A61K 7/06; A61K 9/12
[52] U.S. Cl. .......... 424/47; 424/70.11; 424/70.1; 424/195.1; 424/70.21; 424/70.22; 424/70.27; 424/70.31; 514/945; 132/202
[58] Field of Search ............. 424/47, 70.11, 424/70.1, 195.1, 70.21, 70.22, 70.27, 70.31; 514/945; 132/202

[56] References Cited

U.S. PATENT DOCUMENTS

| | | | |
|---|---|---|---|
| 4,237,253 | 12/1980 | Jacquet et al. | 526/75 |
| 4,393,886 | 7/1983 | Strasilla et al. | 132/7 |
| 4,814,101 | 3/1989 | Schieerstein et al. | 102/357 |
| 4,842,849 | 6/1989 | Grollier et al. | 424/70 |
| 4,865,774 | 9/1989 | Fabry et al. | 252/554 |
| 4,931,218 | 6/1990 | Schenker et al. | 252/551 |
| 5,294,726 | 3/1994 | Behler et al. | 554/98 |
| 5,631,003 | 5/1997 | Mueller et al. | 424/70.31 |

FOREIGN PATENT DOCUMENTS

| | | |
|---|---|---|
| 0047714 | 3/1982 | European Pat. Off. |
| 0217274 | 4/1987 | European Pat. Off. |
| 283817 | 9/1988 | European Pat. Off. |
| 337354 | 10/1989 | European Pat. Off. |
| 0502616 | 9/1992 | European Pat. Off. |
| 2817369 | 10/1978 | Germany |
| 3216687 | 12/1982 | Germany |
| 3723354 | 1/1989 | Germany |
| 3725030 | 2/1989 | Germany |
| 3833658 | 4/1990 | Germany |
| 3926344 | 2/1991 | Germany |
| 3929973 | 3/1991 | Germany |
| 4232506 | 3/1994 | Germany |
| 4232512 | 3/1994 | Germany |
| 4234405 | 4/1994 | Germany |
| 4234413 | 4/1994 | Germany |
| 4327699 | 2/1995 | Germany |
| 7773485 | 6/1977 | Japan |
| 2104091 | 3/1983 | United Kingdom |
| 9206778 | 4/1992 | WIPO |
| 9513863 | 5/1995 | WIPO |

OTHER PUBLICATIONS

Cationic denatured proteins as bases for cosmetics, Essential Oils, cosmetics vol. 90, 1979 p. 381.

*Primary Examiner*—Raj Bawa
*Attorney, Agent, or Firm*—Wayne C. Jaeschke; Real J. Grandmaison; Glenn E.J. Murphy

[57] ABSTRACT

A water-based composition for the treatment of hair or skin containing an active-substance combination of cosmetic components consisting of (a) an alkyl polyglycoside corresponding to general formula (I):

$$RO-(Z)_x \qquad (I)$$

in which R is an alkyl radical containing 6 to 22 carbon atoms, Z is a mono- or oligosaccharide and x is a number of 1.1 to 5, or adducts thereof with 1 to 10 moles of ethylene oxide or propylene oxide, (b) a polymer, and (c) a vegetable oil selected from kukui nut oil, almond oil, walnut oil, peach kernel oil, avocado oil, tea tree oil, soya oil, sesame oil, sunflower seed oil, tsubaki oil, evening primrose oil, rice bran oil, palm kernel oil, mango kernel oil, meadow foam oil, thistle oil, macadamia nut oil, grape seed oil, apricot kernel oil, babassu oil, olive oil, wheat germ oil, pumpkin seed oil, mallow oil, hazel nut oil, safflower oil, jojoba oil, canola oil, sasanqua oil and shea butter.

15 Claims, No Drawings

SKIN AND HAIR AEROSOL FOAM PREPARATIONS CONTAINING AN ALKYL POLYGLYCOSIDE AND VEGETABLE OIL

BACKGROUND OF THE INVENTION

1. Field of the Invention

This invention relates to preparations for the treatment of the skin and hair containing a special combination of active substances.

The washing and care of hair is an important part of personal hygiene.

Both the washing of hair with shampoos and the decorative treatment of hair, for example by coloring or permanent waving, are actions which influence the natural structure and properties of the hair. Thus, following a such treatment, the wet and dry combability, hold and body of the hair, for example, can be unsatisfactory or the number of so-called split ends can be increased. In addition, uniform distribution of the dyes applied with hair colorants is often problematical.

Accordingly, it has long been standard practice to subject the hair to a special aftertreatment. To this end, the hair is treated with special active substances, for example quaternary ammonium salts or special polymers, in the form of a rinse. Depending on the formulation used, this treatment improves, for example, the combability, hold and body of the hair, reduces the number of split ends or improves color distribution.

In addition, so-called combination preparations have recently been developed with a view to reducing the effort involved in standard multistage processes, particularly where they are directly applied by the consumer.

In addition to the usual components, for example for cleaning the hair, these preparations additionally contain active substances which previously were reserved for hair aftertreatment preparations. Accordingly, the consumer saves one application step. At the same time, packaging costs are reduced because one product less is used.

The active substances available both for separate aftertreatment formulations and for combination preparations still cannot meet all consumer requirements. In particular, there is a continuing need for active substances and combinations thereof which combine greater effectiveness with ready biodegradability. In addition, color retention is still problematical when the colored hair is washed repeatedly with standard shampoos.

Finally, many hair treatment formulations inevitably come into contact with the scalp. This can result in irritation, particularly in sensitive people. Accordingly, there is still a need to formulate the hair treatment preparations in such a way that there is no risk of scalp irritation. Ideally, the hair treatment preparations should even have a "caring" effect on the scalp.

It has now surprisingly been found that preparations containing a combination of three classes of active substance already known for the treatment of hair effectively satisfy the requirements stated above. In particular, very good dry and wet combability is achieved. In the case of colored hair, a good levelling effect with surprisingly high color retention is in addition achieved. Moreover, a caring effect on the scalp was observed. Finally, preparations in which almost all the components are readily biodegradable can be formulated with this combination of active substances.

DESCRIPTION OF THE INVENTION

Accordingly, the present invention relates to a water-containing skin or hair treatment preparation containing standard cosmetic components, characterized in that it contains a combination of active substances consisting of an alkyl polyglycoside corresponding to general formula (I):

$$RO-(Z)_x \qquad (I)$$

in which R is an alkyl radical containing 6 to 22 carbon atoms,

Z is a mono- or oligosaccharide and x is a number of 1.1 to 5, or adducts thereof with 1 to 10 molecules of ethylene oxide and/or propylene oxide, a polymer and a vegetable oil.

All three classes of active substance are well-known ingredients of hair treatment preparations.

Combinations of alkyl glycosides and polymers and also known, for example from DE-OS 32 16 687, from EP-A1 337 354 and from German patent applications P 42 32 512.9, P 42 32 506.4, P 42 34 413.1 and P 42 34 405.0.

However, there is nothing in this prior art to suggest that advantageous effects could be obtained by using the three-component combination according to the invention in hair and skin treatment preparations.

The first component of the active-substance combination according to the invention are alkyl polyglycosides corresponding to formula (I).

The compounds corresponding to formula (I) are characterized by the following parameters.

The alkyl radical R contains 6 to 22 carbon atoms and may be both linear and branched. Primary, linear and 2-methyl-branched aliphatic radicals are preferred. Corresponding alkyl radicals are, for example 1-octyl, 1-decyl, 1-lauryl, 1-myristyl, 1-cetyl and 1-stearyl. 1-Octyl, 1-decyl, 1-lauryl, 1-myristyl are particularly preferred. Where so-called "oxoalcohols" are used as starting materials, compounds containing an uneven number of carbon atoms in the alkyl chain predominate.

The alkyl glycosides suitable for use in accordance with the invention may contain only one specific alkyl radical R. However, these compounds are normally prepared from natural fats and oils or mineral oils. In this case, mixtures corresponding to the starting compounds or to the particular working up of these compounds are present as the alkyl radicals R.

Particularly preferred alkyl polyglycosides are those in which R consists essentially of $C_8$ and $C_{10}$ alkyl groups, essentially of $C_{12}$ and $C_{14}$ alkyl groups, essentially of $C_8$ to $C_{16}$ alkyl groups or essentially of $C_{12}$ to $C_{16}$ alkyl groups.

Any mono- or oligosaccharides may be used as the sugar unit Z. Sugars containing 5 or 6 carbon atoms and the corresponding oligosaccharides are normally used. Corresponding sugars are, for example, glucose, fructose, galactose, arabinose, ribose, xylose, lyxose, allose, altrose, mannose, gulose, idose, talose and sucrose. Preferred sugar units are glucose, fructose, galactose, arabinose and sucrose, glucose being particularly preferred.

The alkyl polyglycosides suitable for use in accordance with invention contain on average 1.1 to 5 sugar units. Alkyl glycosides in which x has a value of 1.1 to 1.6 are preferred, alkyl glycosides in which x has a value of 1.1 to 1.4 being most particularly preferred.

The alkoxylated homologs of the alkyl polyglycosides mentioned may also be used in accordance with the invention. These homologs may contain on average up to 10 ethylene oxide and/or propylene oxide units per alkyl glycoside unit. These products also are not normally individual compounds, but instead have a corresponding homolog distribution according to the ethoxylation process selected. Corresponding alkoxylated compounds may be obtained, for example, by using ethoxylated fatty alcohols for the synthesis of the alkyl polyglycosides.

The alkyl polyglycosides are present in the preparations according to the invention in quantities of preferably 0.5 to 20% by weight, based on the preparation as a whole. However, quantities of 10% by weight or more are normally only used in special shampoo formulations. In other formulations, quantities of alkyl polyglycosides of 0.5 to 5% by weight are particularly preferred.

The second component of the active-substance combination according to the invention is a polymer. It may be both a cationic, amphoteric, zwitterionic or anionic polymer and a nonionic polymer. It may also be of advantage to use representatives of various polymer types in conjunction with one another.

The cationic polymers suitable use in accordance with the invention contain cationic groups within the polymer chain. These groups may be part of the polymer chain although they may also be positioned inside chains which are connected to a main chain by intermediate links. Typical cationic groups contain quaternary nitrogen or phosphorus atoms. Groups containing quaternary nitrogen atoms are preferred. The quaternary nitrogen atoms may bear both four different or partly identical substituents or may be part of a ring system. Preferred cationic groups are ammonium or imidazolinium groups.

If the ionic groups are situated in the side chains, the polymers are synthesized from compounds which contain at least one polymerizable group in addition to at least one cationic group and which are free from anionic groups.

The polymerizable group is preferably a vinyl group. However, cationic polymers in which the main polymer chain is made up, for example, of glycosides or is protein-like in character may also be used.

Cationic copolymers containing at least one nonionic monomer in addition to the cationic monomers are also preferred for the purposes of the invention. Suitable nonionic monomers are, for example, vinyl pyrrolidone, vinyl acetate, acrylamide, methacrylamide, methyl acrylate, ethyl acrylate, methyl methacrylate and ethyl methacrylate. Vinyl pyrrolidone is a particularly preferred nonionic monomer.

Various cationic polymers suitable for hair care are known to the expert and are commercially available.

The following are examples of such polymers:

Quaternized cellulose derivatives commercially obtainable under the names of CELQUAT® and Polymer JR®. The compounds CELQUAT® 100, CELQUAT®L 200 and POLYMER JR® 400 are preferred quaternized cellulose derivatives.

Quaternized guar derivatives which are commercially available under the names of COSMEDIA GUAR® and JAGUAR®. Preferred guar derivatives are, for example, COSMEDIA GUAR® C-261 and JAGUAR® C 13-S.

Copolymers of vinyl pyrrolidone with quaternized derivatives of dialkyl aminoacrylate and methacrylate, for example vinyl pyrrolidoneldimethyl aminomethacrylate copolymers quaternized with diethyl sulfate and vinyl pyrrolidone/methacrylamidopropyl trimethylammonium chloride copolymers. Such compounds are commercially available under the names of GAFQUAT® 734, GAFQUAT® 755 and GAFQUAT® HS100.

Copolymers of vinyl pyrrolidone with vinyl imidazolinium methochloride commercially available under the name of LUVIQUAT®.

Polymeric dimethyl diallylammonium salts and copolymers thereof with esters and amides of acrylic acid and methacrylic acid. The products commercially available under the names of MERQUAT® 100 (poly-(dimethyl diallylammonium chloride)) and MERQUAT® 550 (dimethyl diallylammonium chloride/acrylamide copolymer) are examples of such cationic polymers.

Cationically derivatized silicone oils, for example the commercially available products Q2-7224 (manufacturer: Dow Corning; a stabilized trimethyl silyl amodimethicone), Dow Corning 929 Emulsion (containing a hydroxylamino-modified silicone which is also known as—Amodimethicone), SM-2059 (manufacturer: General Electric), SLM-55067 (manufacturer: Wacker) and ABI®-QUAT 3270 and 7232 (manufacturer: Th. Goldschmidt; diquaternary polydimethyl siloxanes, Quaternium-80).

Cationically derivatized protein hydrolyzates obtainable, for example, by reaction of alkali-, acid- or enzyme-hydrolyzed proteins with glycidyl trialkylammonium salts or 3-halo-2-hydroxypropyl trialkylammonium salts are also cationic polymers in the context of the present invention.

The proteins, which serve as starting materials for the protein hydrolyzates, may be both of animal origin and of vegetable origin. Typical starting materials are, for example, keratin, collagen, elastin, soya protein, milk protein, wheat protein, silk protein and almond protein. Mixtures with molecular weights of around 100 to around 50,000 dalton are formed by the hydrolysis process. Typical average molecular weights are in the range from about 500 to about 5,000 dalton. Further particulars of cationic derivatization can be found inter alia in Japanese patent application 77/73485 (Chemical Abstracts 90:174508v).

The cationically derivatized protein hydrolyzates advantageously contain one or two long alkyl chains containing 8 to 22 carbon atoms and, correspondingly, two or one short alkyl chain containing 1 to 4 carbon atoms. Compounds containing one long alkyl chain are preferred.

Preferred protein derivatives are substances corresponding to formula (II):

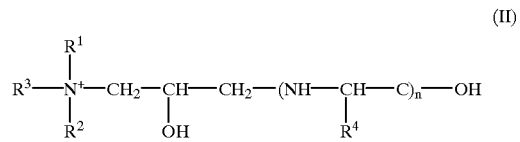

in which $R^4$ represents the side chains of the amino acids of the protein, $R^1$ and $R^2$ independently of one another represent alkyl chains containing 1 to 4 carbon atoms and $R^3$ represents an alkyl chain containing 8 to 22 carbon atoms.

A commercially available product is LAMEQUAT®L (Chemische Fabrik Grünau). It has the following structure:

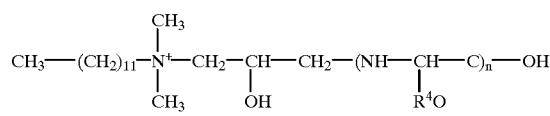

in which R represents the side chains of the amino acids of collagen.

The CTFA name is Lauryldimonium Hydroxypropylamino Hydrolyzed Collagen.

Polymeric condensation resins of polyols and polyamines, for example the polyglycol/polyamine condensation resins known by the CTFA name of PEG-15 Cocopolyamine. The product POLYQUAT®)H 81 (Henkel) is commercially obtainable.

In the context of the invention "amphoteric polymers" are understood to be polymers which contain both free amino groups and free —COOH or —SO$_3$H groups in the molecule and which are capable of forming inner salts. "Zwitterionic polymers" are polymers which contain quaternary ammonium groups and —COO$^-$ or —SO$_3^-$ groups in the molecule.

Examples of amphoteric polymers suitable for use in accordance with the invention are the acrylic resins obtainable under the names of AMPHOMER® and AMPHOMER® LV-71, the copolymers of tert.butyl aminoethyl methacrylate, N-(1,1,3,3-tetramethylbutyl)-acrylamide and two or more monomers from the group consisting of acrylic acid, methacrylic acid or simple esters thereof.

Other amphoteric or zwitterionic polymers which may be used in accordance with the invention are the compounds mentioned in GB 2,104,091, in EP 47 714, in EP 217 274, in EP 238 817 and in DE 28 17 369.

Particular preference is attributed to zwitterionic polymers essentially consisting of (α) monomers containing quaternary ammonium groups corresponding to general formula (III):

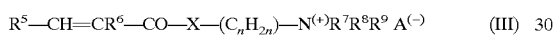

$$R^5-CH=CR^6-CO-X-(C_nH_{2n})-N^{(+)}R^7R^8R^9\ A^{(-)} \qquad (III)$$

in which $R^5$ and $R^6$ independently of one another represent hydrogen or a methyl group and $R^7$, $R^8$ and $R^9$ independently of one another represent alkyl groups containing 1 to 4 carbon atoms, X is an NH group or an oxygen atom, n is an integer of 2 to 5 and $A^{(-)}$ is the anion of an organic or inorganic acid and (β) monomeric carboxylic acids corresponding to general formula (IV):

$$R^{10}-CH=CR^{11}-COOH \qquad (IV)$$

In which $R^{10}$ and $R^{11}$ independently of one another represent hydrogen or methyl groups, or the alkali metal, alkaline earth metal, aluminium or ammonium salts of these acids.

Particulars of the production of these polymers can be found in DE-A 39 29 973.

Polymers based on monomers of the (α) type, in which $R^7$, $R^8$ and $R^9$ are methyl groups, X is an NH group and $A^{(-)}$ is a halide, methoxysulfate or ethoxysulfate ion, are most particularly preferred. Acrylamidopropyl trimethylammonium chloride and methacrylamidopropyl trimethylammonium chloride are particularly preferred monomers (α). Acrylic acid or an alkali metal salt of acrylic acid, more particularly the sodium salt, is preferably used as monomer (β) for the polymers mentioned.

Zwitterionic polymers in which the number of monomers of the (α) type is greater the number of monomers of the (β) type are also preferred. Ratios of monomers of the (α) type to monomers of the (β) type of greater than 1.5 are particularly preferred.

Other preferred zwitterionic polymers are polysiloxane/polyorganobetaine copolymers and also the zwitterionic cellulose ethers according to DE-OS 38 33 658.

Anionic polymers suitable for the purposes of the invention are inter alia:

Vinyl acetate/crotonic acid copolymers commercially available, for example, under the names of RESYN® (National Starch), LUVISET® (BASF) and GAFSET® (GAF). LUVISET® CA-66 is a particularly preferred anionic polymer.

Vinyl pyrrolidone/vinyl acrylate copolymers obtainable, for example, under the name of LUVIFLEX® (BASF). A preferred polymer is the vinyl pyrrolidone/acrylate terpolymer obtainable under the name of LUVIFLEX® VBM-35 (BASF).

Vinyl acetate/butyl maleate/isobornyl acrylate copolymers obtainable under the name of ADVANTAGE® (GAF). ADVANTAGE® CP is a preferred polymer.

Methyl vinyl ether/maleic anhydride copolymers and esters thereof which are obtainable, for example, under the name of GANTREZ® (GAF). GANTREZ® ES 225 is a preferred anionic polymer.

Acrylic acid/ethyl acrylate/N-tert.butyl acrylamide terpolymers marketed, for example, under the name of ULTRAHOLD® 8 (BASF).

Uncrosslinked, partly crosslinked and crosslinked polyacrylic acids, polyacrylic acid esters, acrylic acid/methacrylic acid copolymers and acrylic acid/acrylamide copolymers obtainable, for example, under the names of CARBOPOL®, LATEROLL®, PEMULEN® and ACRYSOL®.

The following are examples of suitable nonionic polymers:

Polyvinyl pyrrolidones, for example the products commercially available under the names of LUVISKOL® K 30 and LUVISKOL® K 90 (BASF).

Vinyl pyrrolidone/vinyl acetate copolymers marketed, for example, under the name of LUVISKOL® (BASF). LUVISKOL® VA 64, LUVISKOL® VA 73 and LUVISKOL® VA 37 are preferred nonionic polymers; LUVISKOL® VA 37 is particularly preferred.

Vinyl pyrrolidoneldimethyl aminoethyl methacrylate/vinyl caprolactam terpolymers obtainable, for example, under the name of Copolymer VC-713 (GAF).

Cellulose ethers, for example hydroxyethyl cellulose, hydroxypropyl cellulose, methyl hydroxypropyl cellulose and hydroxymethyl cellulose.

Among the polymers the cationic, zwitterionic, amphoteric and nonionic are preferred. The cationic polymers and, in particular, the nonionic polymers have proved to be most particularly suitable for the purposes of the invention.

The preparations according to the invention preferably contain 0.05 to 5% by weight and, more particularly, 0.05 to 2% by weight of polymers, based on the preparation as a whole.

Finally, the third component of the active-substance combination according to the invention is a vegetable oil. Examples of vegetable oils suitable for use in accordance with the invention are kukui nut oil, (sweet) almond oil, walnut oil, peach kernel oil, avocado oil, tea tree oil, soya oil, sesame oil, sunflower seed oil, tsubaki oil, evening primrose oil, rice bran oil, palm kernel oil, mango kernel oil, meadow foam oil, thistle oil, macadamia nut oil, grape seed oil, apricot kernel oil, babassu oil, olive oil, wheat germ oil, pumpkin seed oil, mallow oil, hazel nut oil, safflower oil, jojoba oil, canola oil, sasanqua oil and shea butter. Of these oils, soya oil, sesame oil, sunflower seed oil, meadow foam oil, thistle oil, apricot kernel oil, babassu oil, wheat germ oil, jojoba oil and, in particular, kukui nut oil, (sweet) almond oil, peach kernel oil, avocado oil, evening primrose oil, macadamia nut oil and mallow oil are preferred. Macadamia nut oil and, in particular, kukui nut oil have proved to be particularly suitable.

The preparations according to the invention may also contain any of the cosmetic components typical of the particular type of preparation. Of these, the various types of surfactants are mentioned in particular:

Suitable anionic surfactants for the preparations according to the invention are any anionic surfactants suitable for use on the human body. These are characterized by a water-solubilizing anionic group, for example a carboxylate, sulfate, sulfonate or phosphate group, and a lipophilic alkyl group containing around 10 to 22 carbon atoms. In addition, glycol or polyglycol ether groups, ester, ether and amide groups and also hydroxyl groups may be additionally present in the molecule. The following are examples of suitable anionic surfactants—in the form of their sodium, potassium, magnesium and ammonium salts and their mono-, di- and trialkanolammonium salts containing two or three carbon atoms in the alkanol group:

linear fatty acids containing 10 to 22 carbon atoms (soaps), ether carboxylic acids corresponding to the formula R—O—$(CH_2$—$CH_2O)_x$—$CH_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyhydroxyethyl esters containing 8 to 18 carbon atoms in the alkyl group and 1 to 6 hydroxyethyl groups, linear alkanesulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—O$(CH_2$—$CH_2O)_x$—$OSO_3H$, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of adducts of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and also sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups.

Zwitterionic surfactants are surface-active compounds containing at least one quaternary ammonium group and at least one —$COO^{(-)}$ or —$SO_3^{(-)}$ group in the molecule. Particularly suitable zwitterionic surfactants are the so-called betaines, such as N-alkyl-N,N-dimethylammonium glycinates, for example cocoalkyl dimethylammonium glycinate, N-acylaminopropyl-N,N-dimethylammonium glycinates, for example cocoacylaminopropyl dimethylammonium glycinate, and 2-alkyl-3-carboxymethyl-3-hydroxyethyl imidazo-lines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocoamidopropyl Betaine.

Ampholytic surfactants are surface-active compounds which contain at least one free amino group and at least one -COOH or -$SO_3H$ group in addition to a $C_{8-18}$ alkyl or acyl group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethylaminopropionate and $C_{12-18}$ acyl sarcosine.

Examples of cationic surfactants suitable for use in the preparations according to the invention are, in particular, quaternary ammonium compounds. Preferred cationic surfactants are ammonium halides, especially chlorides and bromides, such as alkyl trimethylammonium chlorides, dialkyl dimethylammonium chlorides and trialkyl methylammonium chlorides, for example cetyl trimethylammonium chloride, stearyl trimethylammonium chloride, distearyl dimethylammonium chloride, lauryl dimethylammonium chloride, lauryl dimethyl benzylammonium chloride and tricetyl methylammonium chloride. Other suitable cationic surfactants are so-called esterquats (for example STEPANTEX® VS 90, DEHYQUART®) AU 36 and AU 56) and amidoamines (for example TEGOAMID® S 18).

Nonionic surfactants contain, for example, a polyol group, a polyalkylene glycol ether group or a combination of a polyol and polyglycol ether group as the hydrophilic group. Such compounds are, for example, adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group, $C_{12-22}$ fatty acid monoesters and diesters of adducts of 1 to 30 moles of ethylene oxide with glycerol, adducts of 5 to 60 moles of ethylene oxide with castor oil and hydrogenated castor oil.

The compounds containing alkyl groups used as surfactants may be individual substances. In general, however, it is preferred to use native vegetable or animal raw materials in the production of these substances so that mixtures with different alkyl chain lengths, depending on the particular raw material, are obtained.

In the case of the surfactants representing adducts of ethylene and/or propylene oxide with fatty alcohols or derivatives of these adducts, it is possible to use both products with a "normal" homolog distribution and those with a narrow homolog distribution. By "normal" homolog distribution are meant mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. It can be of advantage to use products with a narrow homolog distribution ("narrow-range" products).

The preparations according to the invention preferably contain surfactants in quantities of 0.5 to 20% by weight, based on the particular preparation.

Besides water, the preparations according to the invention may contain ethanol and isopropanol in particular as further solvents in quantities of up to 20% by weight, based on the preparation as a whole. Quantities of 5 to 10% by weight are particularly preferred.

The preparations according to the invention preferably have a pH value of 2.5 to 7.5 and, more particularly, in the range from 3.5 to 6.5. In certain cases, a pH value of 4.0 to 5.0 can be particularly preferred. Higher pH values, but generally not above 10, may be preferred solely for special products, such as colorants and permanent-wave preparations.

Virtually any acid suitable for cosmetic purposes may be used to adjust this pH value. Edible acids are normally used, especially in cases where the preparation is not a permanent wave preparation. Edible acids are understood to be acids which are ingested in the normal course of eating and which have positive effects on the human organism. Examples of edible acids are acetic acid, lactic acid, tartaric acid, citric acid, malic acid, ascorbic acid and gluconic acid. Citric acid and lactic acid are particularly preferred for the purposes of the invention.

Finally, other typical ingredients of the preparations according to the invention include:

thickeners, such as agar agar, guar gum, alginates and xanthan gum, structurants, such as glucose and maleic acid, protein hydrolyzates, more particularly elastin, collagen, keratin, milk protein, soya protein and wheat protein hydrolyzates and condensates thereof with fatty acids, perfume oils, dimethyl isosorbide and cyclodextrins, solubilizers, such as ethylene glycol, propylene glycol, glycerol and diethylene glycol, dyes, anti-dandruff agents, such as Piroctone Olamine and Zinc Omadine, other pH regulators, active substances, such as panthenol, allantoin, pyrrolidone carboxylic acids, vegetable extracts and vitamins, light stabilizers, consistency regulators, such as sugar esters, polyol esters and polyol alkyl ethers, fats and waxes, such a spermaceti, beeswax, montan wax, paraffins and fatty alcohols, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, opacifiers, such as latex, pearlescers, such as ethylene glycol monostearate and distearate, and antioxidants.

The active-substance combinations according to the invention develop their positive effects in all typical skin and hair treatment preparations. However, they are used with particular advantage in hair-cleaning and hair-care preparations. Corresponding preparations are, in particular, shampoos, hair rinses, hair aftertreatment preparations, hair conditioners and hair setting preparations.

The preparations suitable for use in accordance with the invention may be formulated as solutions, lotions, emulsions, microemulsions, creams or gels. They are preferably formulated as solutions, emulsions or microemulsions with a water content of 50 to 90% by weight, based on the preparation as a whole.

In another preferred embodiment, the preparations may be formulated as foam aerosols. In this case, they may be formulated both with a liquefied gas as propellent and in the form of so-called pump sprays in which the pressure required for spraying is built up by mechanical pumping. Nitrogen, air, carbon dioxide, propane, butane, isobutane, pentane and dimethyl ether are preferred propellents. Although chlorofluorocarbons and chlorinated hydrocarbons are excellent propellents in regard to the aerosol properties obtained, their use as propellents in the preparations according to the invention is less preferred on account of the well-known ozone problems.

The present invention also relates to the use of the preparations according to the invention for the treatment of the hair or skin.

The preparations used in accordance with the invention may remain both on the skin and on the hair. Skin creams, skin lotions, sunscreens, hair aftertreatment preparations, hair tonics and hair setting preparations are examples of preparations used in this way.

However, the preparations according to the invention may also be used in such a way that the preparation is rinsed off the hair or the skin after a contact time of a few seconds to a few minutes. Skin cleansing preparations, hair shampoos, hair rinses and hair tonics are examples of such preparations.

The following Examples are intended to illustrate the invention.

EXAMPLES

I. Colorimetric Studies of Color Retention in Colored Hair

Method

A leveling tress (natural white, 2 g, about 15 cm long; obtainable from Kerling) was tied in the middle. To simulate seriously damaged hair, the lower part of the tress was alternately cold-waved and bleached twice. Cold waving was carried out by treatment with an aqueous solution of a cold-wave formulation based on ammonium thioglycolate (30 minutes) and subsequent fixing with potassium bromate solution (10 minutes). Bleaching was carried out with an aqueous solution of hydrogen peroxide and ammonium peroxydisulfate. To simulate lightly damaged hair, the upper part of the tress was only bleached once. The entire tress was then colored with the commercial product Poly Diadem Pflege Intensiv Tönung (shade: mahogany/coral) (HENKEL). 4 g of coloring mixture were used per g of hair tress. After a contact time of 30 minutes, the tress was thoroughly rinsed with warm water (30° C.) and dried with a hair dryer. The colored hair tress was then stored for 2 days at room temperature.

After calorimetric determination of the zero value, the towel-dry hair tress was treated for 2 minutes with 0.3 g of test mixture per g of hair in the case of preparations to be rinsed off. The tress was then thoroughly rinsed with water (30° C.), dried and calorimetrically measured. Before the next application, the tress was washed with a commercially available shampoo and dried.

In the case of formulations intended to remain on the hair, 0.3 g of test mixture per g of hair was applied to the towel-dry hair tress. The tress was then combed through once and left overnight to dry. On the next day, the tress was calorimetrically measured. Before the next application, the tress was washed with a commercially available shampoo and dried.

The measurement was carried out with a Datacolor Tex-flash using type D65 light (daylight). To this end, the sample to be measured was fixed in a clamp to the spectral photometer and the reflectance values were measured over the visible light range of 390 to 700 nm at intervals of 10 nm and processed in a computer. The computer program determined the standard color values under the CIE system (Commission Internationale de L'Eclairage) in accordance with DIN 5033 and converted them into color difference values according to DIN 6174. The values shown for the total color difference DE (relative to the zero value) are average values from 4 measurement points per tress half.

The following three mixtures according to the invention and corresponding comparison mixtures were investigated:
E1 /C1: hair rinse (is rinsed off)
E2 /C2: tube tonic (remains on the hair)
E3 /C3: foam tonic (remains on the hair)

The compositions of the mixtures investigated and the measurement results are set out in Table 1.

All quantities are percentages by weight. In the data relating to the total color difference DE, N stands for the number of applications of the preparation and DD for the degree of damage to the hair.

TABLE 1

| Component | E1 | C1 | E2 | C2 | E3 | C3 |
|---|---|---|---|---|---|---|
| STENOL ® 1618[1] | 2.4 | 1.8 | — | — | — | — |
| TEGOAMID ® S 18[2] | 1.6 | 1.6 | — | — | — | — |
| CUTINA ® CP[3] | 0.8 | 1.0 | — | — | — | — |
| AJIDEW ® N 50[4] | 0.5 | 0.5 | — | — | — | — |
| Citric acid | 0.7 | 0.5 | — | — | — | — |
| Diisopropyl adipate | — | — | 0.8 | 0.8 | 0.8 | 0.8 |
| CREMOPHOR ® RH 40[5] | — | — | 0.1 | 0.1 | 0.1 | 0.1 |
| LUVISKOL ® 90[6] | — | — | 0.1 | 0.1 | 0.1 | 0.1 |
| CELQUAT ® 200[7] | — | — | 0.5 | 0.5 | 0.5 | 0.5 |
| SEPIGEL ® 305[8] | — | — | 3.0 | 3.0 | 1.0 | 1.0 |
| DOW CORNING ® 345[9] | — | — | — | — | 0.2 | 0.2 |
| PLANTAREN ® 1200[10] | — | — | — | — | 1.0 | 1.0 |
| KUKUI NUT | 0.8 | — | 0.4 | — | 0.2 | — |
| Ethanol | — | — | 12.0 | 12.0 | — | — |
| Water | ← ad 100 → | | | | | |
| DE (n/DD) | | | | | | |
| -1/Serious | 2.3 | 3.4 | 1.5 | 1.8 | 1.5 | 2.7 |
| -3/Serious | 8.9 | 9.5 | 7.3 | 9.5 | 7.8 | 11.0 |
| -1/Slight | 0.9 | 1.5 | 0.9 | 1.9 | 0.5 | 0.7 |
| -3/Slight | 4.2 | 4.3 | 4.7 | 5.1 | 4.8 | 5.2 |

[1]$C_{16/18}$ fatty alcohol (HENKEL)
[2]N,N-dimethyl-N'-stearoyl-1,3-diaminopropane(CFTA name: Stearamidopropyl Dimethylamin)(GOLDSCHMIDT)
[3]Ester of saturated long-chain fatty alcohols and fatty acids) mainly palmitic acid cetyl ester (CTFA name: Cetyl Palmitate)(HENKEL)
[4]DL-2-pyrrolidone-5-carboxylic acid sodium salt (approx. 50% active substance; CTFA name: Sodium PCA)(AJINOMOTO)
[5]Castor Oil hydrogenated + 45 ethylene oxide (CTFA name: PEG-40 Hydrogenated Castor Oil)(BASF)
[6]Polyvinyl pyrrolidone (BASF)
[7]Hydroxyethyl cellulose/diallyl dimethylammonium chloride (95% active substance; CTFA name: Polyquaternium-4)(DELFT NATIONAL)
[8]Dodecyl alcohol + 7EO/isoparaffin/polyacrylamide mixture (CTFA name: Polyacrylamide (and) C13–14-Isoparaffin (and) Laureth-7)(SEPPIC)
[9]Dimethyl cyclosiloxane pentamer (CTFA name: Cyclomethicone) (DOW CORNING)
[10]$C_{12-16}$ alkyl glucoside, degree of oligomerization 1.4 (approx. 50% active substance; CTFA name: Lauryl Polyglycosid)(HENKEL)

What is claimed is:

1. A water-based foam aerosol composition having a pH of 2.5 to 7.5 for the treatment of hair or skin containing cosmetic components consisting essentially of
    (a) an alkyl polyglycoside corresponding to general formula (I):

$$RO{-}(Z)_x \qquad (I)$$

in which R is an alkyl radical containing 6 to 22 carbon atoms, Z is a mono- or oligosaccharide and x is a number of 1.1 to 5, or alkoxylated homologs thereof containing 1 to 10 moles of ethylene oxide or propylene oxide,
    (b) 0.05% to 5% by weight of a polymer selected from the group consisting of a cationic, amphoteric, zwitterionic, anionic and nonionic polymer, and
    (c) a vegetable oil selected from kukui nut oil, almond oil, walnut oil, peach kernel oil, avocado oil, tea tree oil, soya oil, sesame oil, sunflower seed oil, tsubaki oil, evening primrose oil, rice bran oil, palm kernel oil, mango kernel oil, meadow foam oil, thistle oil, macadamia nut oil, grape seed oil, apricot kernel oil, babassu oil, olive oil, wheat germ oil, pumpkin seed oil, mallow oil, hazel nut oil, safflower oil, jojoba oil, canola oil, sasanqua oil and shea butter.

2. A composition as in claim 1 wherein in formula (I), Z is glucose, R is an alkyl radical containing 8 to 18 carbon atoms and x is a number of 1.1 to 1.6.

3. A composition as in claim 1 wherein said polymer is a nonionic polymer.

4. A composition as in claim 1 wherein said vegetable oil is selected from kukui nut oil, almond oil, peach kernel oil, avocado oil, evening primrose oil, macadamia nut oil and mallow oil.

5. A composition as in claim 4 wherein said vegetable oil is kukui nut oil or macadamia nut oil.

6. A composition as in claim 1 containing 0.5% to 20% by weight of said alkyl polyglycoside and 0.1% to 5% by weight of said vegetable oil.

7. A composition as in claim 1 wherein a propellent gas selected from the group consisting of nitrogen, air, carbon dioxide, propane, butane, isobutane, pentane and dimethyl ether is present in said foam aerosol.

8. The process of treating hair or skin comprising contacting said hair or skin with a water-based foam aerosol composition having a pH of 2.5 to 7.5 containing cosmetic components consisting essentially of
    (a) an alkyl polyglycoside corresponding to general formula (I):

$$RO{-}(Z)_x \qquad (I)$$

in which R is an alkyl radical containing 6 to 22 carbon atoms, Z is a mono- or oligosaccharide and x is a number of 1.1 to 5, or alkoxylated homologs thereof containing 1 to 10 moles of ethylene oxide or propylene oxide,
    (b) 0.05% to 5% by weight of a polymer selected from the group consisting of a cationic, amphoteric, zwitterionic, anionic and nonionic polymer, and
    (c) a vegetable oil selected from kukui nut oil, almond oil, walnut oil, peach kernel oil, avocado oil, tea tree oil, soya oil, sesame oil, sunflower seed oil, tsubaki oil, evening primrose oil, rice bran oil, palm kernel oil, mango kernel oil, meadow foam oil, thistle oil, macadamia nut oil, grape seed oil, apricot kernel oil, babassu Oil, olive oil, wheat germ oil, pumpkin seed oil, mallow oil, hazel nut oil, safflower oil, jojoba oil, canola oil, sasanqua oil and shea butter.

9. A process as in claim 8 wherein in formula (I), Z is glucose, R is an alkyl radical containing 8 to 18 carbon atoms and x is a number of 1.1 to 1.6.

10. A process as in claim 8 wherein said polymer is a nonionic polymer.

11. A process as in claim 8 wherein said vegetable oil is selected from kukui nut oil, almond oil, peach kernel oil, avocado oil, evening primrose oil, macadamia nut oil and mallow oil.

12. A process as in claim 11 wherein said vegetable oil is kukui nut oil or macadamia nut oil.

13. A process as in claim 8 wherein said composition contains 0.5% to 20% by weight of said alkyl polyglycoside and 0.1% to 5% by weight of said vegetable oil.

14. A process as in claim 8 wherein a propellent gas selected from the group consisting of nitrogen, air, carbon dioxide, propane, butane, isobutane, pentane and dimethyl ether is present in said foam aerosol.

15. A process as in claim 8 including rinsing said composition off the hair or skin after a contact time of a few seconds to a few minutes.

* * * * *